(12) United States Patent
Wake et al.

(10) Patent No.: US 9,610,120 B2
(45) Date of Patent: Apr. 4, 2017

(54) HIGH-FREQUENCY TREATMENT TOOL FOR ENDOSCOPE

(71) Applicant: OLYMPUS CORPORATION, Tokyo (JP)

(72) Inventors: Fuminori Wake, Yokohama (JP); Yuji Sakamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/858,764

(22) Filed: Sep. 18, 2015

(65) Prior Publication Data

US 2016/0008063 A1     Jan. 14, 2016

Related U.S. Application Data

(63) Continuation of application No. PCT/JP2014/077070, filed on Oct. 9, 2014.

(30) Foreign Application Priority Data

Oct. 9, 2013   (JP) ................................ 2013-212061

(51) Int. Cl.
    *A61B 18/14*        (2006.01)
    *A61B 17/3203*     (2006.01)
    *A61B 18/00*        (2006.01)

(52) U.S. Cl.
    CPC ...... *A61B 18/1492* (2013.01); *A61B 17/3203* (2013.01); *A61B 2018/00077* (2013.01);
(Continued)

(58) Field of Classification Search
    CPC ...... A61B 18/1492; A61B 2018/00494; A61B 2018/00196; A61B 2018/00982;
(Continued)

(56) References Cited

U.S. PATENT DOCUMENTS 9,237,918 B2 *   1/2016   Yamamoto ....... A61B 17/00234
9,387,034 B2 *   7/2016   Okada ................... A61B 18/14
(Continued)

FOREIGN PATENT DOCUMENTS

EP         2322109 A1    5/2011
JP      H11114060 A    4/1999
(Continued)

OTHER PUBLICATIONS

Dec. 16, 2014 International Search Report issued in International Patent Application No. PCT/JP2014/077070.

*Primary Examiner* — Michael Peffley

(74) *Attorney, Agent, or Firm* — Oliff PLC

(57) ABSTRACT

A high-frequency treatment tool for an endoscope includes: a sheath formed of a material having an insulation property; a shaft-shaped member formed of a material having conductivity and inserted to advance and retract in the sheath; and an electrode having a conduit line formed to jet forward a fluid supplied into the sheath, and connected to a distal end section of the shaft-shaped member. The electrode has an outer circumferential surface electrically connected to a contacted tissue to perform treatment, and an inner circumferential surface of the conduit line that faces the fluid when the fluid is supplied. An arithmetic average roughness of the outer circumferential surface is larger than an arithmetic average roughness of the inner circumferential surface, and the arithmetic average roughness of the inner circumferential surface is 0.1 μm or less.

7 Claims, 8 Drawing Sheets

(52) U.S. Cl.
CPC ............... *A61B 2018/00083* (2013.01); *A61B 2018/00196* (2013.01); *A61B 2018/00494* (2013.01); *A61B 2018/00589* (2013.01); *A61B 2018/00601* (2013.01); *A61B 2018/00982* (2013.01); *A61B 2018/1405* (2013.01); *A61B 2018/1472* (2013.01); *A61B 2018/1475* (2013.01); *A61B 2218/002* (2013.01)

(58) Field of Classification Search
CPC .. A61B 2018/00589; A61B 2018/1405; A61B 2018/1472; A61B 2018/00077; A61B 2018/1475; A61B 2018/00601
See application file for complete search history.

(56) References Cited

U.S. PATENT DOCUMENTS

| | | | |
|---|---|---|---|
| 2004/0210215 | A1 | 10/2004 | Okada |
| 2010/0111708 | A1 | 5/2010 | Seto et al. |
| 2012/0035607 | A1 | 2/2012 | Karwei |
| 2014/0207134 | A1* | 7/2014 | Wake ..................... A61B 18/14 606/39 |

FOREIGN PATENT DOCUMENTS

| | | | |
|---|---|---|---|
| JP | 2001178740 | A | 7/2001 |
| JP | 2004167081 | A | 6/2004 |
| JP | 2006115966 | A | 5/2006 |
| JP | 2009240380 | A | 10/2009 |
| JP | 2010042155 | A | 2/2010 |
| JP | 2010106748 | A | 5/2010 |
| JP | 2012075618 | A | 4/2012 |
| JP | 2012523863 | A | 10/2012 |

* cited by examiner

HIGH-FREQUENCY TREATMENT TOOL FOR ENDOSCOPE

CROSS REFERENCE TO RELATED APPLICATIONS

This application is a continuation application based on a PCT Patent Application No. PCT/JP2014/077070, filed Oct. 9, 2014, whose priority is claimed on Japanese Patent Application No. 2013-212061, filed Oct. 9, 2013, the entire content of which are hereby incorporated by reference.

BACKGROUND OF THE INVENTION

Field of the Invention

The present invention relates to a high-frequency treatment tool for an endoscope capable of jetting a fluid forward while incising a biological tissue or the like.

Description of the Related Art

In the related art, treatment using a high-frequency treatment tool for an endoscope capable of jetting a liquid medicine, saline, or the like, from a distal end section while endoscopically incising a biological tissue such as a mucosa or the like is performed. As the above high-frequency treatment tool for an endoscope, for example, treatment tools disclosed in Japanese Unexamined Patent Application, First Publication No. H11-114060 (hereinafter referred to as Patent Literature 1) and Japanese Unexamined Patent Application, First Publication No. 2001-178740 (hereinafter referred to as Patent Literature 2) are known.

In the high-frequency treatment tool for an endoscope of Patent Literature 1, a hollow electrode is connected and fixed to a distal end of an inner tube inserted to advance and retract in a mantle tube in an axial direction. Accordingly, as the inner tube advances and retracts in the mantle tube in the axial direction, the hollow electrode protrudes from the distal end of the mantle tube.

A stopper formed of a metal ring configured to restrict excessive protrusion of the hollow electrode is disposed at an inner surface near the distal end of the mantle tube. In addition, a flange section protruding from an outer circumferential surface is formed at a rear half section of the hollow electrode. When the hollow electrode extends from the distal end of the mantle tube by a predetermined length and the flange section abuts the stopper, the hollow electrode does not protrude further from distal end of the mantle tube. A conductive wire is inserted in the inner tube, and a distal end of the conductive wire is connected to the vicinity of the rear end section of the hollow electrode.

In the above-mentioned high-frequency treatment tool for an endoscope, the liquid medicine (a fluid) can be sent from an injector to the hollow electrode via the inner tube. A high frequency voltage can be applied to the hollow electrode via the conductive wire by a high frequency power supply.

When the high-frequency treatment tool for an endoscope is used, before the treatment such as injection of a liquid medicine or the like is terminated and the hollow electrode is extracted from the mucosa, the high frequency voltage is applied to the hollow electrode to cauterize and solidify the mucosa around the hollow electrode. As a result, even when the hollow electrode is stuck into a large blood vessel, bleeding from a pinhole after the hollow electrode is extracted can be prevented.

SUMMARY

According to a first aspect of the present invention, a high-frequency treatment tool for an endoscope includes: a sheath formed of a material having an insulation property; a shaft-shaped member formed of a material having conductivity and inserted to advance and retract in the sheath; and an electrode having a conduit line formed to jet forward a fluid supplied into the sheath, and connected to a distal end section of the shaft-shaped member, wherein the electrode has an outer circumferential surface electrically connected to a contacted tissue to perform treatment, an inner circumferential surface of the conduit line that faces the fluid when the fluid is supplied, and an arithmetic average roughness of the outer circumferential surface is larger than an arithmetic average roughness of the inner circumferential surface, and the arithmetic average roughness of the inner circumferential surface is 0.1 μm or less, the electrode is a tubular electrode having the conduit line formed along a longitudinal axis of the sheath, and an arithmetic average roughness of a distal end surface of the electrode is larger than the arithmetic average roughness of the inner circumferential surface of the conduit line, and smaller than the arithmetic average roughness of the outer circumferential surface.

According to a second aspect of the present invention, in the high-frequency treatment tool for the endoscope of the first aspect, the outer circumferential surface of the electrode, a distal end surface of the electrode, and the inner circumferential surface of the conduit line may be composed of a surface of the material having conductivity that constitutes the electrode, and the arithmetic average roughness of the inner circumferential surface of the conduit line, which is a polished surface of the material having conductivity, may be ⅙ or less of the arithmetic average roughness of the outer circumferential surface.

According to a third aspect of the present invention, in the high-frequency treatment tool for the endoscope of the first aspect, the electrode may have: an electrode main body that is hollow; and an enveloping layer provided on an inner circumferential surface of the electrode main body.

According to a fourth aspect of the present invention, in the high-frequency treatment tool for the endoscope of the second aspect, the electrode may have a large diameter section disposed at a distal end side and a small diameter section disposed at a proximal end side, the conduit line may be opened at a distal end surface of the large diameter section through the small diameter section, the outer circumferential surface may be formed on an outer circumference of the small diameter section, and an outer circumferential edge section of the distal end surface, which is disposed at a distal end of the large diameter section, may be formed in a curved shape.

According to a fifth aspect of the present invention, in the high-frequency treatment tool for the endoscope of the fourth aspect, in coefficients of friction when the outer circumferential surface of the electrode, the inner circumferential surface of the conduit line and the distal end surface of the electrode may come in contact with a tissue, the coefficient of friction in the outer circumferential surface may be larger than the coefficient of friction in the inner circumferential surface and equal to or more than the coefficient of friction in the distal end surface, and the outer circumferential surface may be configured to incise the tissue in contact with the outer circumferential surface, the coefficient of friction in the distal end surface may be equal to or less than the coefficient of friction in the outer circumferential surface and larger than the coefficient of friction in the inner circumferential surface, and the distal end surface may be configured so that the electrode is moved while the distal end surface comes in contact with the tissue and prevent coagulated object discharged from the conduit line from remaining at the distal end surface, and the coefficient of friction in the inner circumferential surface may be smaller than the coefficient of friction in the outer circumferential surface and the coefficient of friction in the distal end surface, and the coagulated object coagulated on the inner circumferential surface, which is caused by incision of the tissue, may be configured to be exfoliated and discharged owing to supply of the fluid.

According to a sixth aspect of the present invention, in the high-frequency treatment tool for the endoscope according to the fourth or fifth aspect, a length of the electrode may be 1 mm or more and 5 mm or less, and an outer diameter of the small diameter section may be 0.3 mm or more and 0.5 mm or less, and an inner diameter of the conduit line may be 0.2 mm or more and 0.4 mm or less, and a supply pressure of the fluid in a supply port of the fluid in communication with the conduit line may be 100 kPa or more and 3000 kPa or less.

DETAILED DESCRIPTION OF THE PREFERRED EMBODIMENTS

Hereinafter, an embodiment of a high-frequency treatment tool for an endoscope according to the present invention will be described with reference to FIGS. 1 to 16. Further, in all of the following drawings, for the purpose of easy understanding of the drawings, thicknesses of components or the ratio of dimensions may be appropriately varied.

Figure 1:
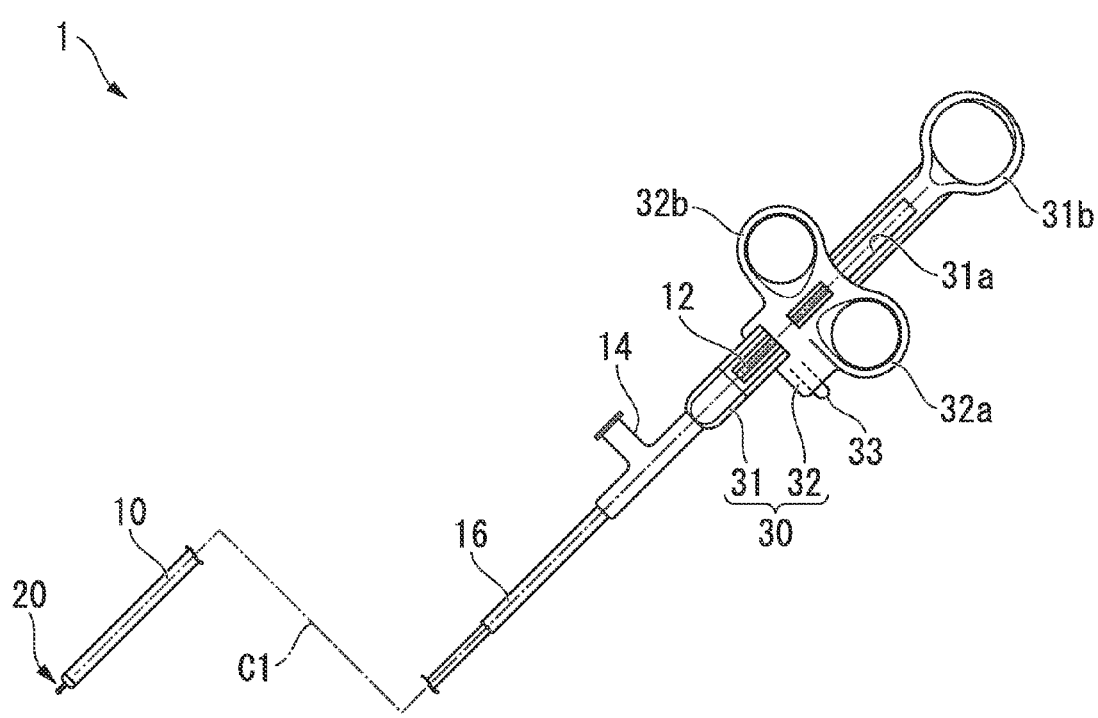
FIG. 1 is a general view of a high-frequency treatment tool for an endoscope according to an embodiment of the present invention.

FIG. 1 is a general view of a high-frequency treatment tool for an endoscope according to the embodiment. As shown in FIG. 1, a high-frequency treatment tool 1 for an endoscope of the embodiment is used in a state in which a flexible insertion section 10 having a treatment section 20 installed at a distal end section thereof is inserted into a channel of an endoscope (not shown).

Figure 2:
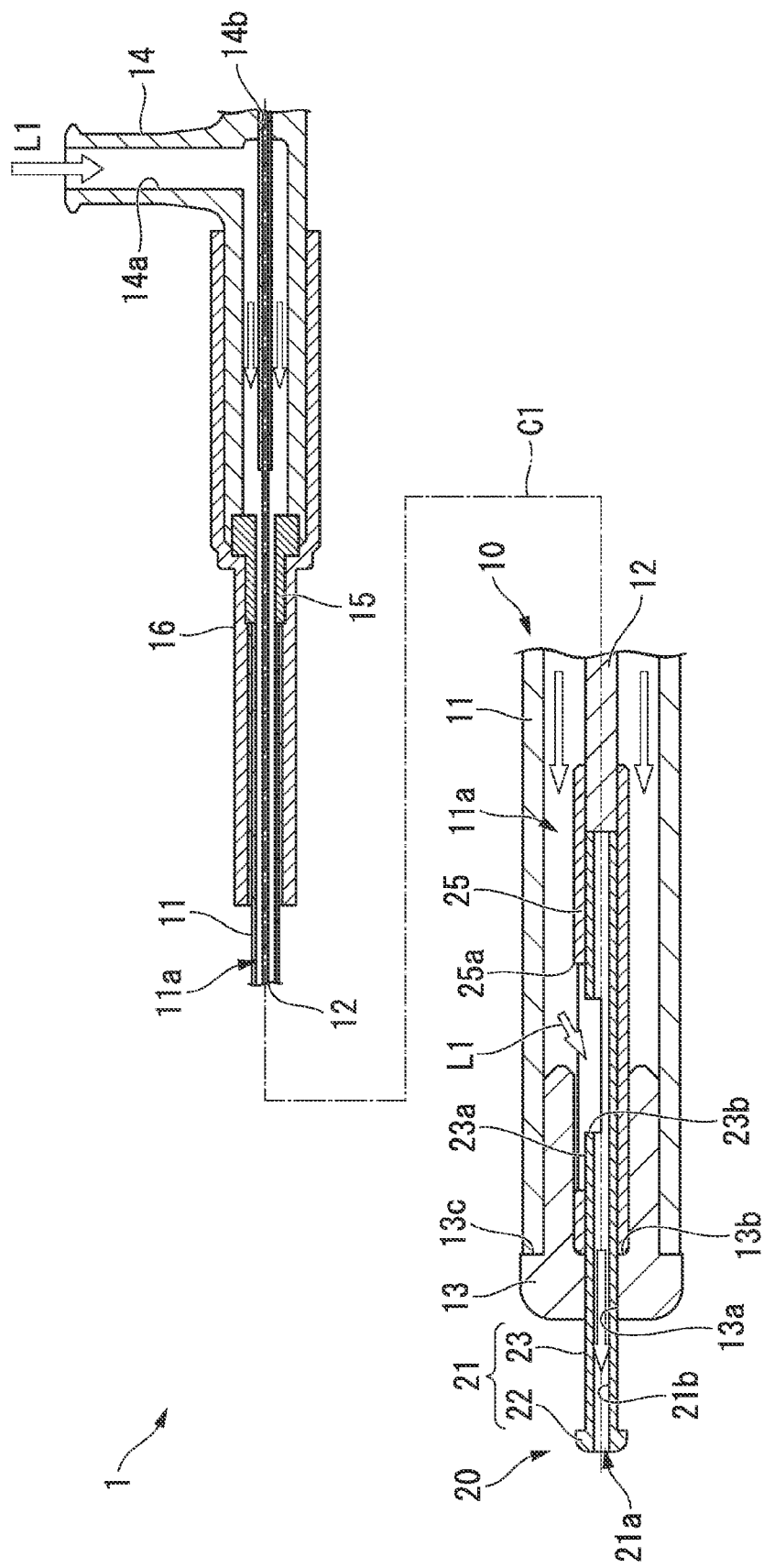
FIG. 2 is a cross-sectional view in an axial direction of a distal end side in a pushed state of the high-frequency treatment tool for an endoscope according to the embodiment of the present invention.

FIG. 2 is a cross-sectional view in an axial direction of a distal end side in a pushed state of the high-frequency treatment tool for an endoscope according to the embodiment. The high-frequency treatment tool 1 for the endoscope according to the embodiment includes a flexible sheath 11, a manipulation wire (a shaft-shaped member) 12 and an electrode member 21.

The sheath 11 is formed of a material having an electrical insulation property, for example, tetrafluoroethylene or the like. An outer diameter of the sheath 11 is set to a size that can be inserted in a channel of an endoscope (not shown). The manipulation wire 12 is inserted to advance and retract in the sheath 11 in a direction along a longitudinal axis C1 of the sheath 11. The manipulation wire 12 is formed of a material having conductivity such as a metal or the like. The sheath 11 and the manipulation wire 12 constitute the insertion section 10 (see FIG. 2) inserted in the channel of the endoscope.

An insulation tip 13 is fixed to a distal end section of the sheath 11 by an adhesive or the like (not shown). The insulation tip 13 is formed of a material having heat resistance and an insulation property such as zirconia, ceramics, or the like, in a cylindrical shape. A cylinder hole 13a in communication with an internal space of the sheath 11 and opened at a distal end is formed in the insulation tip 13. A stepped portion 13b is formed at the cylinder hole 13a of the insulation tip 13 by increasing the diameter of the proximal end side. An outer circumferential stepped portion 13c is formed at the outer circumferential surface of the insulation tip 13 by reducing the diameter of the proximal end side.

The outer diameter of a portion closer to the distal end than the outer circumferential stepped portion 13c of the insulation tip 13 is substantially equal to the outer diameter of the sheath 11. The distal end section of the sheath 11 and the outer circumferential stepped portion 13c of the insulation tip 13 are fixed.

A liquid sending mouth piece 14 is attached to the proximal end section of the sheath 11 via a cylindrical connecting member 15. An injection port (a supply port) 14a in communication with an internal space 11a of the sheath 11 is formed at the liquid sending mouth piece 14. An anti-buckling tube 16 is attached to an outer circumferential surface of a connecting section between the sheath 11 and the liquid sending mouth piece 14. The anti-buckling tube 16 is formed to prevent the proximal end section of the sheath 11 from being broken when the proximal end section of the sheath 11 is curved.

An opening 14b through which the proximal end section of the manipulation wire 12 is inserted is formed at the liquid sending mouth piece 14. A seal material (not shown) is formed in the opening 14b of the liquid sending mouth piece 14. The liquid sending mouth piece 14 and the manipulation wire 12 are water-tightly sealed by the seal material such as an O-ring or the like, and the manipulation wire 12 is supported to advance and retract the manipulation wire 12 with respect to the liquid sending mouth piece 14 in a direction along the longitudinal axis C1. A water feed means such as a water feed tube or the like extending from a syringe or a water feed pump (not shown) is detachably attached to the injection port 14a.

Figure 3:
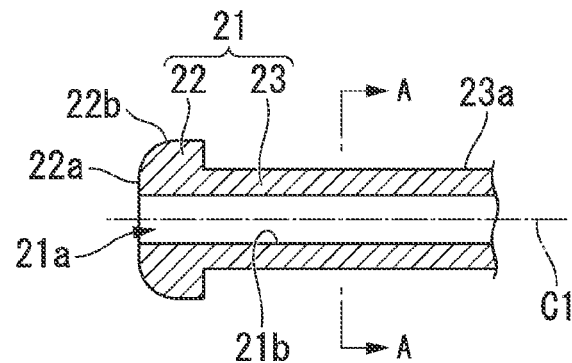
FIG. 3 is an enlarged view of a major part of the electrode member of FIG. 2.

The treatment section 20 has the electrode member (an electrode) 21 that is hollow. FIG. 3 is an enlarged view of a major part of the electrode member of FIG. 2. In the embodiment, as shown in FIGS. 2 and 3, the electrode member 21 is formed in a tubular shape, and the conduit line 21a is formed therein. As shown in FIG. 2, the electrode member 21 is connected to the distal end section of the manipulation wire 12.

A maximum protrusion length of the electrode member 21 from the sheath 11 in the direction along the longitudinal axis C1 (in the embodiment, a maximum protrusion length of the electrode member 21 from the insulation tip 13) is preferably, for example, about 1 mm or more and 5 mm or less because the mucosa tissue is incised and the muscle layer portion is not excised.

The electrode member 21 is formed of a material having conductivity such as stainless steel or the like.

Figure 4:
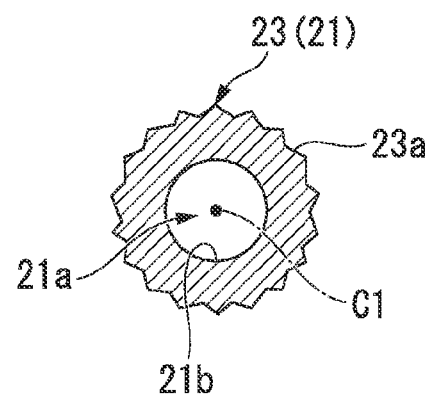
FIG. 4 is a cross-sectional view taken along line A-A of FIG. 3.

FIG. 4 is a cross-sectional view taken along line A-A shown in FIG. 3. As shown in FIGS. 3 and 4, the electrode member 21 has a large diameter section 22 and a small diameter section 23. The large diameter section 22 is disposed at the distal end side of the electrode member 21. The small diameter section 23 is disposed closer to the proximal end than the large diameter section 22, and has a smaller outer diameter than the large diameter section 22. As shown in FIG. 3, an outer circumferential edge section of a distal end surface 22a of the large diameter section 22 is provided to form a circle when seen in a side view.

The outer diameter of the small diameter section 23 is preferably, for example, about 0.3 mm or more and 0.5 mm or less in order to appropriately increase a density of a high-frequency current. The outer diameter of the small diameter section 23 is slightly smaller than the inner diameter of a portion closer to the distal end than the stepped portion 13b in the cylinder hole 13a of the insulation tip 13. The small diameter section 23 of the electrode member 21 is inserted in the cylinder hole 13a of the insulation tip 13.

A conduit line 21a of the electrode member 21 is opened at the distal end surface of the large diameter section 22 through the small diameter section 23. That is, the conduit line 21a of the electrode member 21 passes through the electrode member 21 in the direction along the longitudinal axis C1, and the electrode member 21 is a tubular electrode at which the conduit line 21a is formed along the longitudinal axis C1.

The inner diameter of the conduit line 21a is constant regardless of a position in the direction along the longitudinal axis C1. The inner diameter of the conduit line 21a is preferably, for example, about 0.2 mm or more and 0.4 mm or less to achieve a jet pressure and a jet flow diameter for appropriately injecting saline or a liquid medicine under the mucosa.

As shown in FIG. 2, a communication hole 23b passing from an outer circumferential surface 23a of the small diameter section 23 to an inner circumferential surface is formed at an intermediate section of the small diameter section 23 in the direction along the longitudinal axis C1.

An arithmetic average roughness (Ra) of an outer circumferential surface 22b of the large diameter section 22 and the outer circumferential surface 23a of the small diameter section 23 defined by JIS B0601-1994 is larger (rougher) than an arithmetic average roughness of an inner circumferential surface 21b of the conduit line 21a. The arithmetic average roughness of the inner circumferential surface 21b of the conduit line 21a is 0.1 µm (micrometer) or less, in this example, 0.02 µm. Further, the arithmetic average roughness of the inner circumferential surface 21b is preferably 0.05 µm or less.

The arithmetic average roughness of the outer circumferential surface 22b of the large diameter section 22 and the arithmetic average roughness of the outer circumferential surface 23a of the small diameter section 23 shown in FIGS. 3 and 4 are, for example, 6.3 µm. The arithmetic average roughness of the inner circumferential surface 21b of the conduit line 21a is ⅙ or less of the arithmetic average roughness of the outer circumferential surface 22b of the large diameter section 22, and ⅙ or less of the arithmetic average roughness of the outer circumferential surface 23a of the small diameter section 23.

The arithmetic average roughness of the distal end surface 22a of the large diameter section 22 is larger than the arithmetic average roughness of the inner circumferential surface 21b of the conduit line 21a, equal to or less than the arithmetic average roughness of the outer circumferential surface 22b of the large diameter section 22, and equal to or less than the arithmetic average roughness of the outer circumferential surface 23a of the small diameter section 23. In the embodiment, the arithmetic average roughness of the distal end surface 22a of the large diameter section 22 is, for example, 2.5 µm.

Further, coefficients of friction when the outer circumferential surface 23a of the small diameter section 23, the inner circumferential surface 21b of the conduit line 21a and the distal end surface 22a of the electrode member 21 come in contact with tissues such as the mucosa to be described below or the like are set as follows.

The coefficient of friction in the outer circumferential surface 23a is larger than the coefficient of friction in the inner circumferential surface 21b, and equal to or larger than the coefficient of friction in the distal end surface 22a. The coefficient of friction in the distal end surface 22a is equal to or smaller than the coefficient of friction in the outer circumferential surface 23a, and larger than the coefficient of friction in the inner circumferential surface 21b. The coefficient of friction in the inner circumferential surface 21b is smaller than the coefficient of friction in the outer circumferential surface 23a and the coefficient of friction in the distal end surface 22a.

The electrode member 21 can be formed by, for example, cutting an outer circumferential surface of a proximal end side of a pipe having an outer diameter larger than the large diameter section 22 of the electrode member 21.

For machining of the inner circumferential surface 21b of the conduit line 21a, a known polishing method such as electrolytic polishing using fine abrasive grain, chemical mechanical polishing (CMP), or the like can be appropriately selected and used.

As shown in FIG. 2, a cylindrical stopper member 25 is attached to an outer circumferential surface of the connecting section between the small diameter section 23 and the manipulation wire 12, and the stopper member 25 connects the electrode member 21 and the manipulation wire 12. A through-hole 25a passing through the stopper member 25 from the outer circumferential surface to the inner circumferential surface is formed in the stopper member 25. The through-hole 25a of the stopper member 25 comes in communication with the communication hole 23b of the electrode member 21. The conduit line 21a of the electrode member 21 comes in communication with the internal space 11a of the sheath 11 via the communication hole 23b of the electrode member 21 and the through-hole 25a of the stopper member 25.

The outer diameter of the stopper member 25 is slightly smaller than an inner diameter of a portion closer to the proximal end than the stepped portion 13b in the cylinder hole 13a of the insulation tip 13. The small diameter section 23 and the stopper member 25 inserted in the cylinder hole 13a are configured to advance and retract a range closer to the proximal end than the stepped portion 13b in the cylinder hole 13a as the manipulation wire 12 is advanced and retracted.

In the embodiment, as shown in FIG. 1, the high-frequency treatment tool 1 for the endoscope further includes a manipulation unit 30. The manipulation unit 30 is installed at the proximal end section of the insertion section 10.

The manipulation unit 30 includes a manipulation unit main body 31 and a manipulation slider 32. The manipulation unit main body 31 is fixed to the proximal end section of the liquid sending mouth piece 14. The manipulation slider 32 is slidably installed with respect to the manipulation unit main body 31.

A slit 31a is formed in the manipulation unit main body 31 along the longitudinal axis C1. The manipulation slider 32 is slidable with respect to the manipulation unit main body 31 along the slit 31a. The manipulation unit main body 31 includes a finger hooking ring 31b formed at the proximal end section.

The manipulation slider 32 includes finger hooking rings 32a and 32b arranged in a direction perpendicular to the longitudinal axis C1. The manipulation slider 32 includes a connecting connector section 33. A cord that leads to a high-frequency generator (not shown) is electrically connected to the connecting connector section 33.

The proximal end section of the manipulation wire 12 is electrically connected to the connecting connector section 33 while fixed to the manipulation slider 32.

Next, a motion of the high-frequency treatment tool 1 for the endoscope configured as described above will be described. The high-frequency treatment tool 1 for the endoscope according to the embodiment is manipulated, for example, as a user serving as an operator inserts his/her thumb into the ring 31b of the manipulation unit main body 31 and inserts his/her index finger and middle finger into the rings 32a and 32b of the manipulation slider 32. By this manipulation, the manipulation slider 32 can be slid with respect to the manipulation unit main body 31 in the direction along the longitudinal axis C1 with one hand.

Then, when the manipulation wire 12 is moved (pushed) with respect to the sheath 11 toward the distal end as the manipulation slider 32 is moved with respect to the manipulation unit main body 31 toward the distal end, as the stopper member 25 is locked to the stepped portion 13b of the insulation tip 13 as shown in FIG. 2, the pushed state in which the manipulation wire 12 is pushed toward the distal end is positioned.

In the pushed state, the small diameter section 23 of the electrode member 21 can protrude toward the distal end further than the sheath 11 through the cylinder hole 13a of the insulation tip 13. Saline (a fluid) L1 is supplied into the internal space 11a of the sheath 11 from the injection port 14a of the liquid sending mouth piece 14. The physiological saline solution L1 is supplied into the conduit line 21a of the electrode member 21 through the through-hole 25a of the stopper member 25 and the communication hole 23b of the electrode member 21 to pass through the inner circumferential surface 21b of the conduit line 21a to be jetted in front of the electrode member 21.

Figure 5:
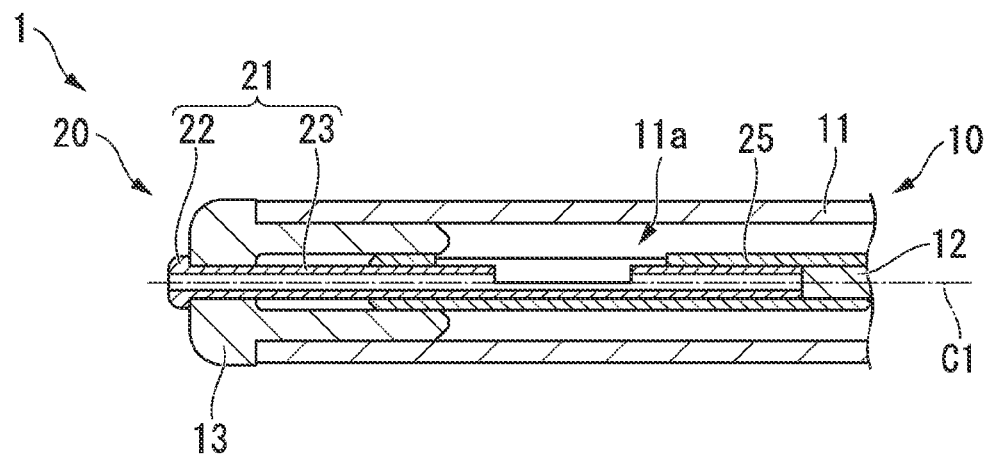
FIG. 5 is a cross-sectional view in the axial direction of the distal end side in a returned state of the high-frequency treatment tool for an endoscope according to the embodiment of the present invention.

FIG. 5 is a cross-sectional view in an axial direction of a distal end side in a returned state of the high-frequency treatment tool 1 for the endoscope according to the embodiment. The manipulation wire 12 is moved (returned) with respect to the sheath 11 toward the proximal end as the manipulation slider 32 is moved with respect to the manipulation unit main body 31 toward the proximal end. As a result, as shown in FIG. 5, the small diameter section 23 of the electrode member 21 is accommodated in the internal space 11a of the sheath 11 and the large diameter section 22 abuts the distal end surface of the insulation tip 13. Accordingly, the returned state in which the manipulation wire 12 is returned to the proximal end side is positioned.

Next, treatment using the high-frequency treatment tool 1 for the endoscope according to the embodiment will be described. Hereinafter, for example, a motion when the mucosa in the body cavity is endoscopically excised using the high-frequency treatment tool 1 for the endoscope according to the embodiment will be described.

First, a counter electrode plate (not shown) is mounted on a patient. The high-frequency treatment tool 1 for the endoscope in the returned state is endoscopically guided into the body cavity through the channel of the endoscope (not shown). Here, the high-frequency treatment tool 1 for the endoscope is guided while the image acquired by the observation unit of the endoscope is observed using the display unit such as a monitor or the like.

The distal end section of the insertion section 10 of the high-frequency treatment tool 1 for the endoscope protrudes from the channel of the endoscope, and the treatment section 20 is opposite to the lesion mucosa portion serving as the target area to be excised in the body cavity.

Figure 6:
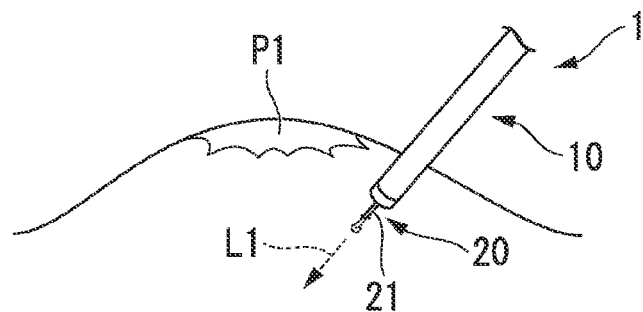
FIG. 6 is a view showing a procedure using the high-frequency treatment tool for an endoscope according to the embodiment of the present invention, showing a state in which a lesion mucosa portion is raised.

A syringe or a water feed tube (not shown) is attached to the injection port 14a of the liquid sending mouth piece 14. A user inserts his/her fingers into the rings 31b, 32a and 32b, pushes the manipulation slider 32 with respect to the manipulation unit main body 31, and causes the high-frequency treatment tool 1 for the endoscope to be in the pushed state to advance the electrode member 21 from the insulation tip 13. FIG. 6 is a view showing a state in which the lesion mucosa portion is raised. As shown in FIG. 6, the electrode member 21 pierces into the vicinity of a lesion mucosa portion P1, and the physiological saline solution L1 accommodated in the syringe or the water feed pump is supplied into the internal space 11a of the sheath 11 to be jetted to the front side from the electrode member 21. The jetted physiological saline solution L1 is injected into the submucosal layer of the lesion mucosa portion P1, and the lesion mucosa portion P1 is raised.

Next, a high-frequency generator (not shown) is connected to the connecting connector section 33 of the manipulation unit 30. A high frequency voltage is applied to the electrode member 21 via the connecting connector section 33 and the manipulation wire 12 by the high-frequency generator. Here, the electrode member 21 reaches a high temperature of about 100° C.

Figure 7:
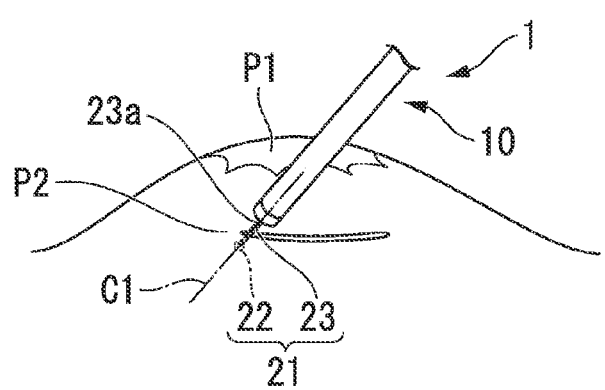
FIG. 7 is a view showing a procedure using the high-frequency treatment tool for an endoscope according to the embodiment of the present invention, showing a state in which the lesion mucosa portion is incised.

FIG. 7 is a view showing a state when the lesion mucosa portion is incised. As shown in FIG. 7, when the electrode member 21 of the high-frequency treatment tool 1 for the endoscope moves in a lateral direction perpendicular to the longitudinal axis C1, a mucosa (a tissue) P2 in contact with the electrode member 21 is incised. The arithmetic average roughness of the outer circumferential surface 23a of the small diameter section 23 is larger than the arithmetic average roughness of the inner circumferential surface 21b of the conduit line 21a, specifically, for example, 6.3 µm. In addition, the coefficient of friction between the outer circumferential surface 23a and the mucosa P2 is set as described above. For this reason, the mucosa P2 is securely caught on the outer circumferential surface 23a of the small diameter section 23, and the mucosa P2 in contact with the outer circumferential surface 23a is incised. In this way, the outer circumferential surface 23a of the small diameter section 23 is configured to be electrically connected to the mucosa P2 in contact with the outer circumferential surface 23a to perform the treatment.

The arithmetic average roughness of the distal end surface 22a of the large diameter section 22 is larger than the arithmetic average roughness of the inner circumferential surface 21b of the conduit line 21a, and equal to or smaller than the arithmetic average roughness of the outer circumferential surface 23a of the small diameter section 23. In addition, the coefficient of friction between the distal end surface 22a and the mucosa P2 is set as described above. For this reason, even when the electrode member 21 is moved in a state in which the distal end surface 22a of the large diameter section 22 comes in contact with the peripheral tissue, the distal end surface 22a applies little load to the tissue.

Figure 8:
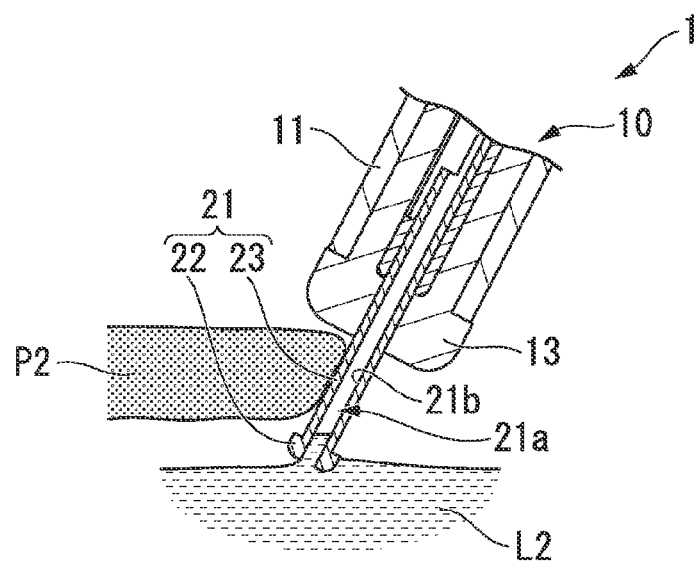
FIG. 8 is a view showing a procedure using the high-frequency treatment tool for an endoscope according to the embodiment of the present invention, showing a state in which a body fluid enters a conduit line of the electrode member.

FIG. 8 is a view showing a state in which the body fluid enters a conduit line of the electrode member. As shown in FIG. 8, when incision of the mucosa P2 or treatment of solidifying a blood point is performed, a body fluid L2 such as blood or the like enters the conduit line 21a of the electrode member 21 from the distal end side through a capillary phenomenon or the like. In this case, the body fluid L2 solidifies at the inner circumferential surface 21b of the conduit line 21a as heat from the electrode member 21 of a high temperature is transferred. Whether the body fluid L2 solidifies in the conduit line 21a can be identified by a force required when the physiological saline solution L1 is supplied by the syringe or electric power required to drive the water feed pump. This is because a flow path area of the conduit line 21a is reduced as the body fluid L2 solidifies at the inner circumferential surface 21b of the conduit line 21a.

Figure 9:
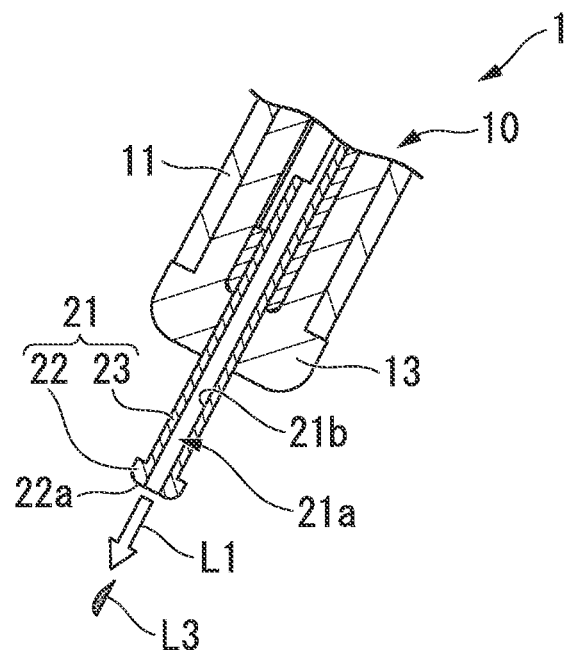
FIG. 9 is a view showing a procedure using the high-frequency treatment tool for an endoscope according to the embodiment of the present invention, showing a state in which saline is jetted from the inside of the conduit line of the electrode member.

FIG. 9 is a schematic view showing a state in which the physiological saline solution L1 is jetted from the inside of the conduit line 21a of the electrode member 21. When the body fluid L2 solidifies at the inner circumferential surface 21b of the conduit line 21a, as shown in FIG. 9, the physiological saline solution L1 is jetted forward at a large pressure through the conduit line 21a of the electrode member 21. The arithmetic average roughness of the inner circumferential surface 21b of the conduit line 21a is 0.1 µm or less, and the coefficient of friction between the inner circumferential surface 21b and the mucosa P2 is set as described above. For this reason, coagulated object L3 of the body fluid L2 coagulated at the inner circumferential surface 21b of the conduit line 21a are peeled off from the inner circumferential surface 21b with the pressure of the physiological saline solution L1 to be discharged. Since the coefficient of friction between the arithmetic average roughness of the distal end surface 22a of the large diameter section 22 and the mucosa P2 is set as described above, the coagulated object L3 discharged from the conduit line 21a can be prevented from remaining on the distal end surface 22a.

Here, the physiological saline solution L1 fed from the syringe or the water feed pump may be supplied at a pressure of about 100 kPa (kilopascals) or more and 3000 kPa or less in the injection port 14a of the liquid sending mouth piece 14. When the supply pressure is less than 100 kPa, exfoliation of the coagulated object L3 may be insufficient. When the supply pressure exceeds 3000 kPa, the sheath 11 may be damaged due to an inflow pressure of the physiological saline solution L1.

Figure 10:
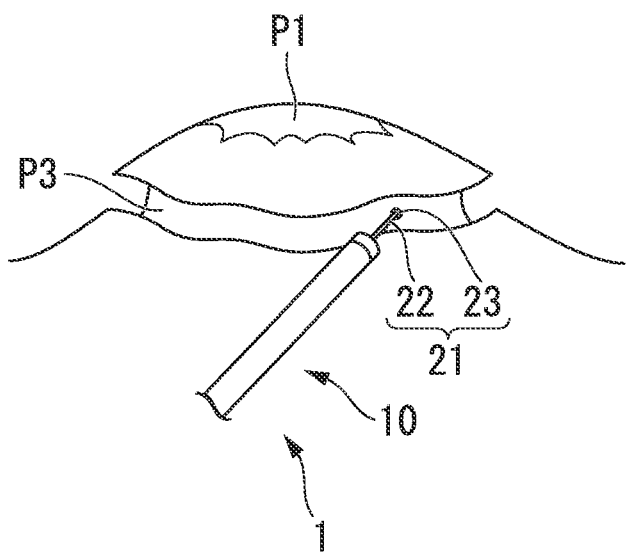
FIG. 10 is a view showing a procedure using the high-frequency treatment tool for an endoscope according to the embodiment of the present invention, showing a state in which the lesion mucosa portion is exfoliated.

FIG. 10 is a view showing a state in which the lesion mucosa portion is exfoliated. When the lesion mucosa portion P1 is completely incised throughout the circumferential direction, as shown in FIG. 10, the electrode member 21 abuts a cut edge P3 obtained by incising a periphery of the lesion mucosa portion P1, and the lesion mucosa portion P1 is sequentially incised to entirely excise and exfoliate the lesion mucosa portion P1.

Next, the high-frequency treatment tool 1 for the endoscope enters the returned state to be extracted from the inside of the channel of the endoscope to the hand side. Grasping forceps (not shown) are inserted in the empty channel of the endoscope. The grasping forceps are manipulated to endoscopically extract the lesion mucosa portion P1 to terminate a series of treatments.

As described above, according to the high-frequency treatment tool 1 for the endoscope of the embodiment, the arithmetic average roughness of the inner circumferential surface 21b of the electrode member 21 is 0.1 µm or less. For this reason, the coagulated object L3 stuck to the inner circumferential surface 21b can be easily exfoliated from the inner circumferential surface 21b at the pressure of the physiological saline solution L1, and can be easily washed away to the outside of the electrode member 21. Accordingly, clogging of the conduit line 21a of the electrode member 21 with the coagulated object L3 can be limited.

In the embodiment, since the arithmetic average roughness of the outer circumferential surface 23a of the small diameter section 23 is larger than the arithmetic average roughness of the inner circumferential surface 21b of the conduit line 21a, the mucosa P2 is securely caught by the outer circumferential surface 23a of the small diameter section 23, and heat is securely transferred from the electrode member 21 having the high temperature to the mucosa P2. Accordingly, the mucosa P2 can be securely incised using the electrode member 21.

Since the arithmetic average roughness of the distal end surface 22a of the large diameter section 22 is larger than the arithmetic average roughness of the inner circumferential surface 21b of the conduit line 21a, machining of the distal end surface 22a of the large diameter section 22 can be relatively easily performed by known polishing or the like. Since the arithmetic average roughness of the distal end surface 22a of the large diameter section 22 is equal to or smaller than the arithmetic average roughness of the outer circumferential surface 23a of the small diameter section 23, the load applied to a peripheral tissue by the distal end surface 22a of the large diameter section 22 can be limited.

As the arithmetic average roughness of the distal end surface 22a of the large diameter section 22 is set as described above, the surface of the large diameter section 22 has an appropriate roughness, slippage of the large diameter section 22 with respect to the tissue or catching of the large diameter section 22 to the tissue cannot easily occur, and control precision of the high-frequency treatment tool 1 for the endoscope becomes better.

Further, while the conduit line 21a is opened to face the distal end surface 22a of the large diameter section 22, as the distal end surface 22a has an appropriate surface roughness, the coagulated object L3 can be securely discharged from the conduit line 21a in a state in which the coagulated object L3 exfoliated from the inner circumferential surface 21b of the electrode member 21 do not remain on the surface of the large diameter section 22.

The electrode member 21 of the high-frequency treatment tool 1 for the endoscope according to the embodiment can be variously deformed.

Figure 11:
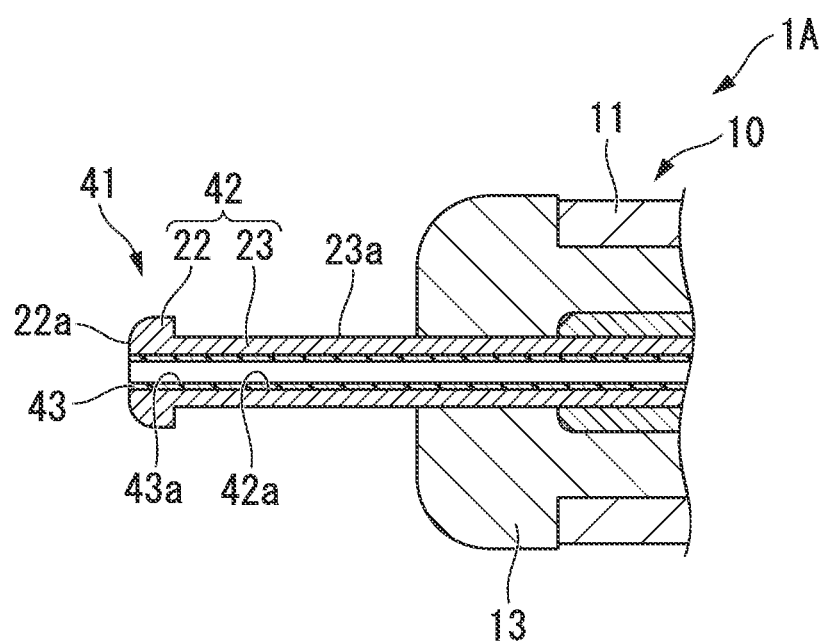
FIG. 11 is a cross-sectional view in an axial direction of a distal end side of a high-frequency treatment tool for an endoscope according to a first variant of the embodiment of the present invention.

For example, FIG. 11 is a cross-sectional view showing a distal end portion of an electrode member 41 of a first variant of the embodiment. Like a high-frequency treatment tool 1A for an endoscope shown in FIG. 11, the electrode member 41 may be provided instead of the electrode member 21 according to the embodiment. The electrode member 41 of the variant is different from the embodiment in that an enveloping layer 43 is formed at an inner circumferential surface 42a of an electrode main body 42.

The enveloping layer 43 may be formed of a material having a heat resistance and a smooth surface, for example, tetrafluoroethylene or the like. An arithmetic average roughness of an inner circumferential surface 43a of the enveloping layer 43 is 0.1 μm or less. In addition, the arithmetic average roughness of the distal end surface 22a of the large diameter section 22 is larger than the arithmetic average roughness of the inner circumferential surface 43a of the enveloping layer 43.

The same effects as the high-frequency treatment tool 1 for the endoscope according to the embodiment can be exhibited even by the high-frequency treatment tool 1A for the endoscope configured as described above.

Figure 12:
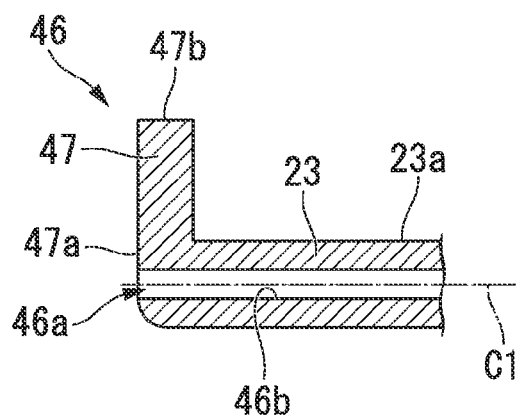
FIG. 12 is a cross-sectional view in an axial direction of an electrode member of a high-frequency treatment tool for an endoscope according to a second variant of the embodiment of the present invention.
Figure 13:
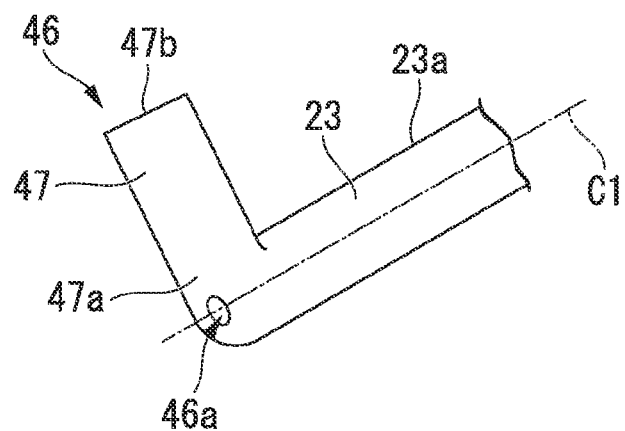
FIG. 13 is a perspective view of the electrode member of the second variant of the embodiment of the present invention.

FIGS. 12 and 13 are cross-sectional views showing a distal end portion of an electrode member 46 of a second variant of the embodiment. Like the electrode member 46 shown in FIGS. 12 and 13, a large diameter section 47 may be formed to extend in only one direction crossing the longitudinal axis C1. In the variant, the electrode member 46 is formed in an L shape as a whole.

In the variant, not only a distal end surface 47a of the large diameter section 47 but also a surface 47b that becomes the distal end in the extending direction of the large diameter section 47 are included in the distal end surface of the electrode member 46 that is hollow. That is, the arithmetic average roughness of each of the distal end surface 47a and the surface 47b of the large diameter section 47 is larger than the arithmetic average roughness of an inner circumferential surface 46b of a conduit line 46a of the electrode member 46, and equal to or less than the arithmetic average roughness of the outer circumferential surface 23a of the small diameter section 23.

Figure 14:
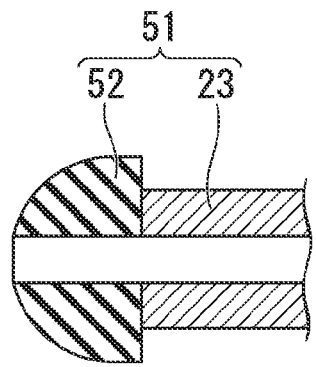
FIG. 14 is a cross-sectional view in an axial direction of an electrode member of a high-frequency treatment tool for an endoscope according to a third variant of the embodiment of the present invention.

FIG. 14 is a cross-sectional view showing a distal end portion of an electrode member 51 of a third variant of the embodiment. Like the electrode member 51 shown in FIG. 14, a large diameter section 52 may be formed in a hemispherical shape having a curved surface protruding toward the distal end side. In this case, as the large diameter section 52 is formed of a material having an insulation property such as a ceramic, the tissue in contact with the distal end surface of the electrode member 51 can be prevented from being incised.

Figure 15:
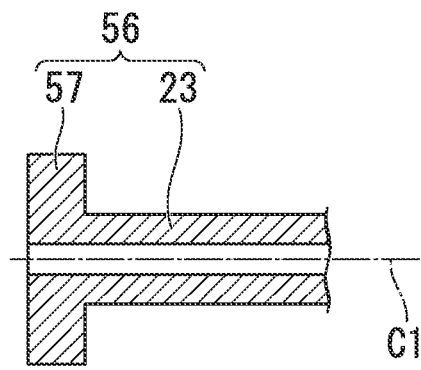
FIG. 15 is a cross-sectional view in an axial direction of an electrode member of a high-frequency treatment tool for an endoscope according to a fourth variant of the embodiment of the present invention.
Figure 16:
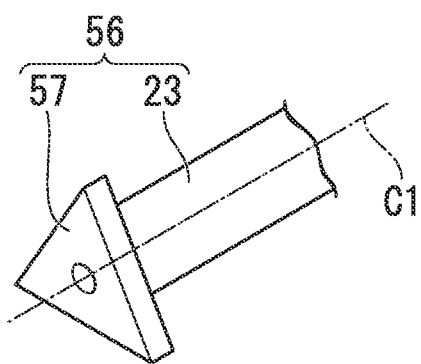
FIG. 16 is a perspective view of the electrode member of the fourth variant of the embodiment of the present invention.

FIG. 15 is a cross-sectional view showing a distal end portion of an electrode member 56 of a fourth variant of the embodiment. FIG. 16 is a perspective view showing the distal end portion of the electrode member 56 of the fourth variant of the embodiment. Like the electrode member 56 shown in FIGS. 15 and 16, a large diameter section 57 is also formed in a triangular plate shape when seen in a direction along the longitudinal axis C1. Further, the shape of the large diameter section when seen in the direction along the longitudinal axis C1 and a direction perpendicular to the longitudinal axis C1 is not limited to the triangular shape but may be a polygonal shape such as a rectangular shape or the like or may be an oval shape.

In the embodiment, the arithmetic average roughness of the distal end surface 22a of the large diameter section 22 is larger than the arithmetic average roughness of the inner circumferential surface 21b of the conduit line 21a, and equal to or smaller than the arithmetic average roughness of the outer circumferential surface 23a of the small diameter section 23. However, the arithmetic average roughness of the distal end surface 22a of the large diameter section 22 may be equal to or smaller than the arithmetic average roughness of the inner circumferential surface 21b of the conduit line 21a, and may be larger than the arithmetic average roughness of the outer circumferential surface 23a of the small diameter section 23.

In the embodiment, while the fluid is the physiological saline solution L1, the fluid is not limited thereto but may be sterilized water, liquid medicine, or the like.

Hereinabove, while the embodiment of the present invention has been described, the technical spirit of the present invention is not limited to the above-mentioned embodiment but combinations of the components of the embodiment may be varied, various modifications may be added to the components, or the components may be deleted without departing from the spirit of the present invention. The present invention is not limited to the above description but is limited only by the scope of the accompanying claims.

What is claimed is:

1. A high-frequency treatment tool for an endoscope comprising:
   a sheath formed of a material having an insulation property;
   a shaft-shaped member formed of a material having conductivity and inserted to advance and retract in the sheath; and
   an electrode having a conduit line formed to jet forward a fluid supplied into the sheath, and connected to a distal end section of the shaft-shaped member,
   wherein the electrode has an outer circumferential surface that is adapted to be electrically connected to a tissue to perform treatment, and an inner circumferential surface of the conduit line that faces the fluid when the fluid is supplied,
   an arithmetic average roughness of the outer circumferential surface is larger than an arithmetic average roughness of the inner circumferential surface, and the arithmetic average roughness of the inner circumferential surface is 0.1 μm or less, the electrode is a tubular electrode having the conduit line formed along a longitudinal axis of the sheath, and an arithmetic average roughness of a distal end surface of the electrode is larger than the arithmetic average roughness of the inner circumferential surface of the conduit line, and smaller than the arithmetic average roughness of the outer circumferential surface.

2. The high-frequency treatment tool for the endoscope according to claim 1, wherein the outer circumferential surface of the electrode, the distal end surface of the electrode, and the inner circumferential surface of the conduit line are composed of a surface of the material having conductivity that constitutes the electrode, and the arithmetic average roughness of the inner circumferential surface of the conduit line, which is a polished surface of the material having conductivity, is ⅙ or less of the arithmetic average roughness of the outer circumferential surface.

3. The high-frequency treatment tool for the endoscope according to claim 1, wherein the electrode has:

an electrode main body that is hollow; and an enveloping layer provided on an inner circumferential surface of the electrode main body.

4. The high-frequency treatment tool for the endoscope according to claim 2, wherein the electrode has a large diameter section disposed at a distal end side and a small diameter section disposed at a proximal end side, the conduit line is opened at a distal end surface of the large diameter section through the small diameter section, the outer circumferential surface is formed on an outer circumference of the small diameter section, and an outer circumferential edge section of the distal end surface, which is disposed at a distal end of the large diameter section, is formed in a curved shape.

5. The high-frequency treatment tool for the endoscope according to claim 4, wherein, in coefficients of friction when the outer circumferential surface of the electrode, the inner circumferential surface of the conduit line and the distal end surface of the electrode come in contact with a tissue, a coefficient of friction in the outer circumferential surface is larger than a coefficient of friction in the inner circumferential surface and equal to or more than a coefficient of friction in the distal end surface, and the outer circumferential surface is configured to incise the tissue in contact with the outer circumferential surface, the coefficient of friction in the distal end surface is equal to or less than the coefficient of friction in the outer circumferential surface and larger than the coefficient of friction in the inner circumferential surface, and the distal end surface is configured so that the electrode is moved while the distal end surface comes in contact with the tissue and prevent coagulated object discharged from the conduit line from remaining at the distal end surface, and the coefficient of friction in the inner circumferential surface is smaller than the coefficient of friction in the outer circumferential surface and the coefficient of friction in the distal end surface, and the coagulated object coagulated on the inner circumferential surface, which is caused by incision of the tissue, are configured to be exfoliated and discharged owing to supply of the fluid.

6. The high-frequency treatment tool for the endoscope according to claim 4, wherein a length of the electrode is between 1 mm and 5 mm, and an outer diameter of the small diameter section is between 0.3 mm and 0.5 mm, and an inner diameter of the conduit line is between 0.2 mm and 0.4 mm, and a supply pressure of the fluid in a supply port of the fluid in communication with the conduit line is 100 kPa or more and 3000 kPa or less.

7. The high-frequency treatment tool for the endoscope according to claim 5, wherein a length of the electrode is between 1 mm and 5 mm, and an outer diameter of the small diameter section is between 0.3 mm and 0.5 mm, and an inner diameter of the conduit line is between 0.2 mm and 0.4 mm, and a supply pressure of the fluid in a supply port of the fluid in communication with the conduit line is 100 kPa or more and 3000 kPa or less.

* * * * *